United States Patent [19]

Roskam

[11] 4,111,785

[45] Sep. 5, 1978

[54] APPARATUS FOR PREPARATIVE ELECTROPHORESIS

[76] Inventor: Willem Gerrit Roskam, 55 Rue Lacordaire, 75015 Paris, France

[21] Appl. No.: 797,286

[22] Filed: May 16, 1977

[30] Foreign Application Priority Data

May 18, 1976 [NL] Netherlands ............................ 7605315

[51] Int. Cl.² ...................... G01N 27/26; G01N 27/28
[52] U.S. Cl. ............................ 204/299 R; 204/180 G
[58] Field of Search ............... 204/180 R, 180 G, 299, 204/301

[56] References Cited

U.S. PATENT DOCUMENTS

| 3,375,187 | 3/1968 | Buchler | 204/299 |
| 3,533,933 | 10/1970 | Strauch | 204/180 G |
| 3,579,433 | 5/1971 | Dahlgren | 204/299 |
| 3,697,406 | 10/1972 | Svendsen | 204/299 |
| 3,704,217 | 11/1972 | Nerenberg | 204/180 G |
| 3,791,950 | 2/1974 | Allington | 204/180 G |

OTHER PUBLICATIONS

Shimada et al., "A New Device of Preparative Polyacrylamide Gel Electrophoresis ... RNA", Anal. Biochem, 51, 456–465 (1973).

Primary Examiner—Arthur C. Prescott
Attorney, Agent, or Firm—Ladas, Parry, Von Gehr, Goldsmith & Deschamps

[57] ABSTRACT

Electrophoresis apparatus comprises a tubular member for receiving a column of gel, and a plate-form body of solid but porous material, such as glass fit, defining an elution chamber at one end of the tubular member. An inlet duct delivers elution buffer into the plate-form body by way of one of the main faces thereof.

23 Claims, 6 Drawing Figures

APPARATUS FOR PREPARATIVE ELECTROPHORESIS

The present invention relates to apparatus for preparative electrophoresis.

Apparatus for preparative electrophoresis usually comprises an upper electrode vessel, a separation space in which a gel can be applied, an elution chamber or receptacle and a lower electrode vessel. The various components of the material to be treated (purified or separated) migrate through the gel under the influence of the applied electric field at different flow rates, so that they emerge one after the other from the gel and enter the elution chamber in turn. A buffer solution flows through the elution chamber and carries the components out of the elution chamber, e.g. to a fraction collector, from which collector they can be removed for further examination.

A great variety in constructions of apparatus for preparative electrophoresis exists, and much attention has been paid to the design of the elution chamber. However, in the apparatus according to the state of the art the elution does not proceed satisfactorily for many purposes. In most prior art devices the bottom of the elution chamber is electrically conductive in order to permit flow of the electric electrophoresis current.

The main reason for poor elution in prior devices is that components, after emerging from the gel, do not remain at the spot where the hydrodynamic transport by the elution buffer is most efficient, because they are subjected to effects of free electrophoresis, convection phenomena and migration caused by gravity.

With respect to the free electophoresis it is necessary for a good elution that the components, after emerging from the gel, migrate out of the vicinity of the gel end under the influence of a rapid free electrophoresis because the flow rate of the elution buffer is low in the gel vicinity (S. Hjerten et al., Anal. Biochem. 27 (1969) 108–129), and consequently the elution proceeds inefficiently near the end of the gel column.

The desired rapid free electrophoresis can be achieved by flowing a buffer having a low ion-strength just along the bottom of the gel (J. W. Nelson et al., ISCO Applications Research Bulletin 19 (1975)).

Apparatus according to the state of the art, wherein a solid porous disc between gel and elution chamber supports the gel, does not give a good elution. This is because the components, after emerging from the gel, must migrate over a long distance before the elution begins, and diffusion is no longer prevented by the gel matrix during the migration, the diffusion giving rise to a strong band widening, while the migration cannot be accelerated by flowing a buffer with a low ionic strength just along the bottom of the gel.

In apparatus according to the state of the art only a high pump (circulation) speed of the elution buffer can prevent components from migrating to the vicinity of the bottom of the elution chamber under the influence of the rapid free electrophoresis necessary on account of the grounds mentioned, or convection phenomena, or gravity. However, a high pump speed of the elution buffer leads inevitably to a strong dilution of the components which is disastrous for many applications. On the other hand it is equally disadvantageous to increase the dimensions of the elution chamber to prevent migration towards the bottom, because this lowers the flow rate of the elution buffer.

According to the state of the art, loss of components in the vicinity of the bottom of the elution chamber by electrophoresis through the bottom of the elution chamber is avoided by positioning a dialysis membrane (for example U.S. Pat. No. 3,773,745), or a semipermeable glass filter (U.S. Pat. No. 3,539,493), or a gel in a buffer having a high ionic strength (German Offenlegungsschrift No. 2,221,242) under the elution chamber, or by passing buffer in counterflow through the bottom of the elution chamber (P. H. Duesberg et al., Anal. Biochem. 11 (1965) 342–361).

However, a good elution is not possible if components are able to migrate to the vicinity of the bottom of the elution chamber, because the flow rate of the elution buffer towards the discharge is much lower in the vicinity of the bottom of the elution chamber than in the center of the elution chamber, for example. Moreover, there is a danger of denaturation, absorption and adsorption of the components if a dialysis membrane forms the bottom of the elution chamber (S. Hjerten et al., loc. cit.).

Apparatus based on the design disclosed by I. Schenkein et al. (Anal. Biochem. 25 (1968) 387–395) has the disadvantage that the free electrophoretic migration of the components is in the opposite direction to the flow of the elution buffer. If in this case the elution chamber has a small volume (vide Dutch Patent application No. 7115364) then voltage gradient in the elution chamber is high and the direction of the voltage gradient is such that the components tend to migrate in the opposite direction to the flow of the elution buffer; due to the latter phenomenon the advantageous effect of the elution chamber having a small volume will be lost.

The present invention may be used to provide a simple apparatus for preparative electrophoresis which can be handled easily, and which apparatus does not have the above mentioned disadvantages, and supplies a good elution both with soft and solid gels, and with components having a high as well as a low free electrophoresis mobility.

According to a first aspect of the present invention there is provided electrophoresis apparatus, comprising a tubular member having first and second ends for receiving a column of gel, means defining an elution chamber at the first end of the tubular member, primary inlet duct means for passing buffer solution into the elution chamber, and outlet duct means for discharging buffer solution from the elution chamber and so disposed with respect to the primary inlet duct means that buffer solution passes from the primary inlet duct means to the outlet duct means substantially perpendicular to the central axis of the tubular member, the chamber-defining means comprising a plate-form body of solid but porous material having two main surfaces extending substantially perpendicular to the central axis of said tubular member, and the apparatus also comprising auxiliary inlet duct means for passing an auxiliary flow of solution into the elution chamber through that main surface of the plate-form body which is further from the second end of the tubular member.

According to a second aspect of the present invention there is provided electrophoresis apparatus, comprising a tubular member having first and second ends for receiving a column of gel, and means defining an elution chamber at the first end of the tubular member, the chamber-defining means comprising a plate-form body of solid but porous material.

According to a third aspect of the present invention there is provided a method of constructing electrophoresis apparatus, wherein a layer of silicone rubber is applied to a plate-form body of solid but porous material, the silicone rubber is vulcanized, and the plate-form member is brought into contact with one end of a tubular member, the vulcanized silicone rubber establishing a seal between the plate-form body and the tubular member.

For a better understanding of the invention, and to show how the same may be carried into effect, reference will now be made, by way of example, to the accompanying drawings in which.

Figure 1:
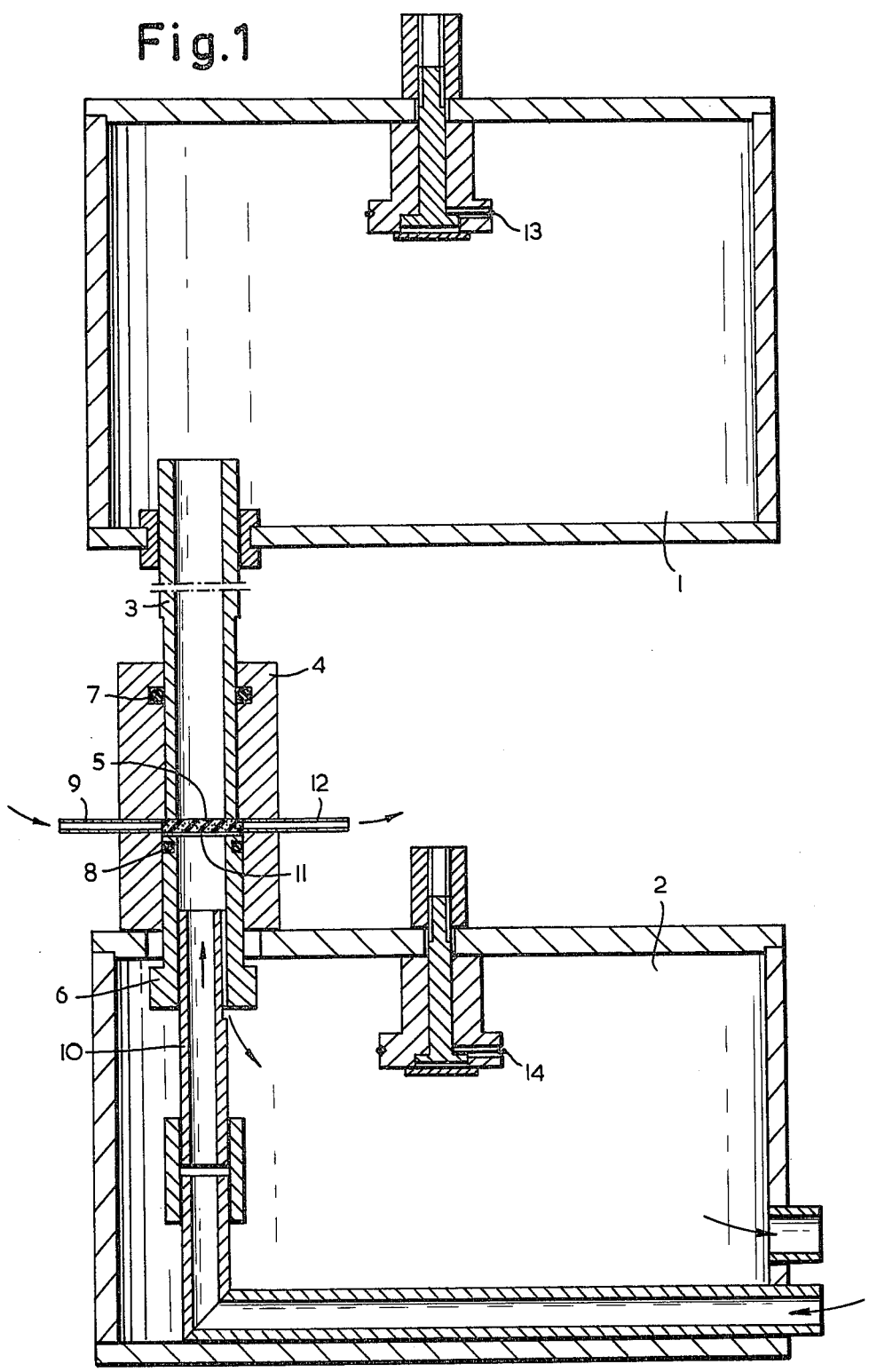
FIG. 1 shows a vertical sectional view of an apparatus for preparative electrophoresis.

The apparatus shown in FIG. 1 comprises an upper electrode vessel 1 provided with an electrode 13, and a lower electrode vessel 2 provided with an electrode 14. The electrodes 13 and 14 are made of platinum wire and are received in circular grooves in respective insulating members, whereby the electrodes are protected from damage. The insulating members are bolted to the upper walls of the vessels 1 and 2 by respective stainless steel nuts and bolts. In order to provide further protection, cylindrical cages may be provided surrounding the insulating members and the electrodes 13 and 14 mounted thereon. The insulating members are formed with radial bores through which connections extend to the electrodes from the stainless steel bolts.

Figure 6:
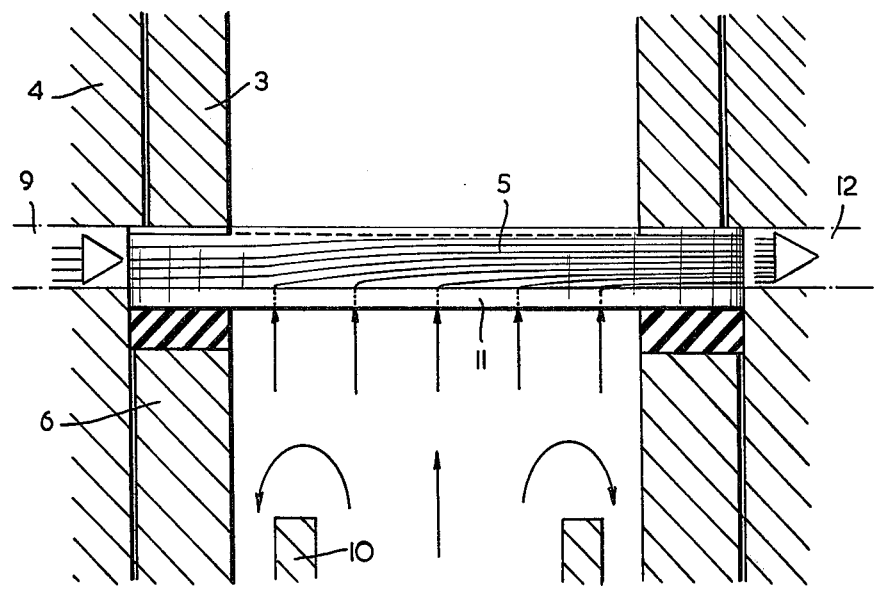
FIG. 6 shows an enlarged sectional view of the apparatus, illustrating flow lines.

Between the vessels 1 and 2 are a cylindrical tube 3 (internal diameter 10 mm) for the gel, a housing 4 for the elution chamber 5 (the latter having a diameter of 15 mm and thickness of 1.5 mm), and a tubular part 6. The elution chamber 5, which has a porous layer 11 at its underside, is located in position by employing the part 6 to press it against an abutment edge in the housing 4. Viton O-rings 7 and 8 are used for ensuring a tight sealed fit of the gel tube 3 and the part 6 in the housing 4. The O-ring 8 not only serves to provide a seal between the part 6 and the housing 4, but also ensures that the part 6 remains correctly positioned in the housing 4. Elution buffers are fed through three stainless steel tubes 9 (only one being shown in FIG. 1) which have been arranged so that an angle of 45° is included between each pair of adjacent tubes 9 (the total angle between the outermost tubes is 90°). An auxiliary flow of elution buffer is delivered to the underside of the porous layer 11 by way of a tube 10. The auxiliary flow, which is at a high rate, serves to cool the elution chamber 5 and the gel. Excess of elution buffer delivered through the tube 10 returns to the electrode vessel 2 via a small spacing between the tube 10 and the part 6 and is recirculated. Flow lines of elution buffer are illustrated in FIG. 6. The electric current for the electrophoresis flows via the mentioned small spacing.

By altering the pumping rate of the buffer flowing through the tube 10, or by altering the spacing between the tube 10 and the part 6, the pressure of the auxiliary flow of elution buffer can be adjusted as desired, and consequently the flow rate of elution buffer through the porous layer 11 into the elution chamber 5 is also adjusted.

The elution buffers are discharged from the elution chamber 5 through a stainless steel tube 12 to an accurately adjustable pump (not shown) and pass from there to a fraction collector e.g. via a spectrophotometer.

The elution chamber 5 is made of solid but porous material such as sintered glass, preferably Pyrex P2; in the illustrated apparatus the liquid volume of the chamber 5 is about 0.13 ml. The porous layer 11 at the underside of the elution chamber may be a dialysis membrane, in which case the auxiliary flow of elution buffer is maintained at high pressure below the membrane. However, the porous layer 11 is preferably a layer of sintered glass of different pore size from the chamber 5, of thickness 0.5 mm, which can advantageously be sintered to the elution chamber. The porous layer 11 is preferably Pyrex P5. The sealing of the elution chamber 5, or if desired the combined elution chamber 5 and porous layer 11, against the gel tube 3, the housing 4 and the part 6 is obtained by forming a suitably-shaped layer of elastic material, preferably polymerized silicone rubber. For this purpose curable silicone rubber, e.g. Rhone Poulenc CAF 4, is applied on the relevant areas of the elution chamber 5, or the combined elution chamber 5 and porous layer 11, and thereafter the assembly is preferably placed in a mould, preferably made of Teflon, for polymerization of the silicone rubber with the sintered glass. Excess silicone rubber is torn away automatically when removing the elution chamber, or the assembly of the elution chamber and the porous layer, from the mould or can be easily removed with a knife and with a tungsten carbide drill at the location of the tubes 9 and 12.

Apart from the stainless steel tubes 9 and 12, the Viton O-rings 7 and 8, the sintered glass elution chamber 5 with its silicone rubber seals, and the porous layer 11, all structural components of the apparatus are made from Perspex (polymethacrylate).

The gel column rests directly on the elution chamber 5 or on a sheet of glass fiber paper on top of the elution chamber, and does not require to be supported by hydrostatic pressure of elution buffer.

The present invention can also be applied profitably on other apparatus, such as apparatus for preparative electrophoresis on a large scale with central elution and cooling of the gel. In such an advantageous embodiment manufacture and control are also simple.

In the described apparatus for preparative electrophoresis, the homogeneous (uniform) buffer flows in the porous elution chamber to prevent the components from reaching the bottom of the elution chamber, whether by convection phenomena, or by a high, free electrophoresis mobility, or by migration caused by gravity, in that it is possible by adapting the ionic strength of the buffer flowing just below the gel, to have the components migrate rapidly out of the vicinity of the gel in that the retarding effect on the electrophoretic migration by the auxiliary buffer, flowing in the opposite direction of migration can be increased by selecting e.g. the ionic strength, pH, viscosity and buffer density. This renders the elution highly efficient, and avoids the disadvantages of components coming into contact with the bottom of the elution chamber.

The porous elution chamber prevents the convection phenomena, migration of the components caused by gravity and preferred paths of the elution buffers in the elution chamber. The elution buffer flows having the above features, are obtained by passing two elution buffers into the elution chamber, one buffer homogeneously distributed on the surface of the elution chamber in a direction opposite the direction of the electrophoresis in the elution chamber and one buffer homogeneously perpendicular at the direction of the electrophoresis. A homogeneous distribution of the elution buffer flow over the surface of the elution chamber is obtained by pumping or by sucking the buffer in question through a porous layer applied against the bottom side of the elution chamber, the flow resistance for the elution buffer being mainly determined by the porous layer.

The above disclosed constructions of the elution chamber and parts belonging thereto simplify the manufacture and handling of apparatus for preparative electrophoresis considerably. The apparatus is flexible and can be adapted in a simple manner to a specific purification process, e.g. by selecting another elution chamber or another housing for the gel. Cooling the gel is simple. The apparatus can be easily cleaned thoroughly, because of its simple construction.

Use of the apparatus will now be described with reference to the following examples:

EXAMPLE I

Samples of a homodisperse $^3$H-poly(U)(tritium-poly(uridine)) mixture were loaded on 3 mm high 9% polyacrylamide gels. Previously it was determined that all radioactivity under the applied conditions would come out of the gel in no less than 8.5 minutes. The sum of the pumping rates of the two elution buffers was varied between 2 and 10 ml. per hour. The pumping rate of the auxiliary flow of elution buffer, passing in counterflow to the direction of the electrophoresis, was maintained constant at 1.5 ml. per hour.

The pumping rate was determined by measuring the transport of $^3$H-water during the electrophoresis. The pumping rate of the auxiliary flow of elution buffer leads to a migration of buffer in the elution chamber with the same speed (rate) as the free electrophoresis of the RNA, but in the opposite direction (couterflow). The voltage gradient in the gel was about 6 V per cm at a current of 10 mA. The concentration of the elution buffers was three times as high as the concentration of the gel buffer except for the sodium dodecyl-suflate concentration being everywhere 0.2%.

Figure 2:
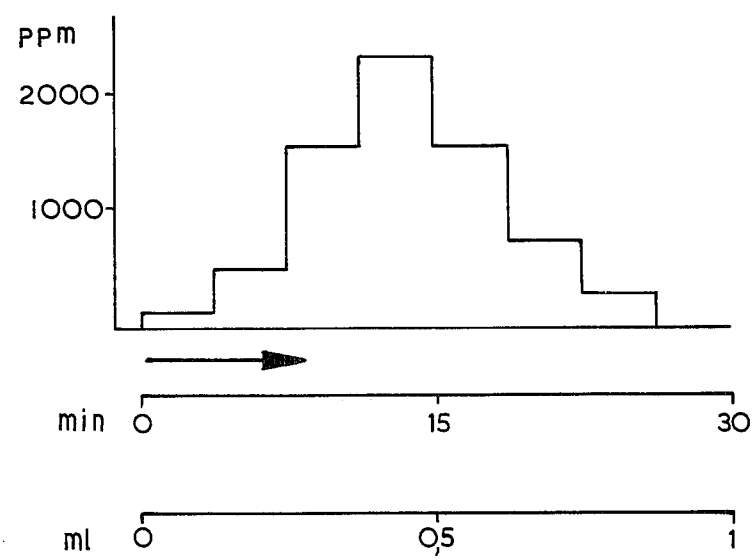
FIGS. 2, 3 and 4 show graphs.

The yields:

By determining the radioactivity in collected fractions it appeared that with about 0.6 ml of elution buffer at all the pumping rates, elution of more than 99% of the radioactivity was obtained, if a correction was made for the bandwidth of the sample. This means that the elution chamber is rinsed by an amount of buffer which is about five times the liquid-volume of the elution chamber, or nine times the liquid-volume of the elution chamber under the gel. In the present calculation no correction has been applied for diffusion in the gel or for band broadening in the tubing leading to the fraction collector; the time elution is thus more efficient than it appears to be. The elution is consequently highly efficient. The yield of radioactivity was always higher than 96%. FIG. 2 shows the variation in radioactivity in the elution buffer at a pumping rate of the elution buffers of 2 ml. per hour. It appears from the form of the curve that elution proceeds quite well at such a low pumping rate, in spite of the high free electrophoresis mobility of RNA.

EXAMPLE II

Figure 3:
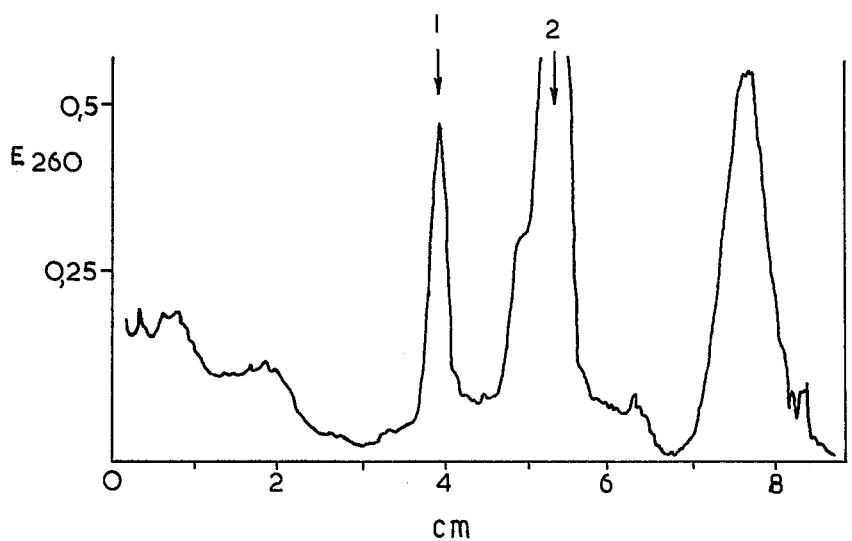
Figure 3:
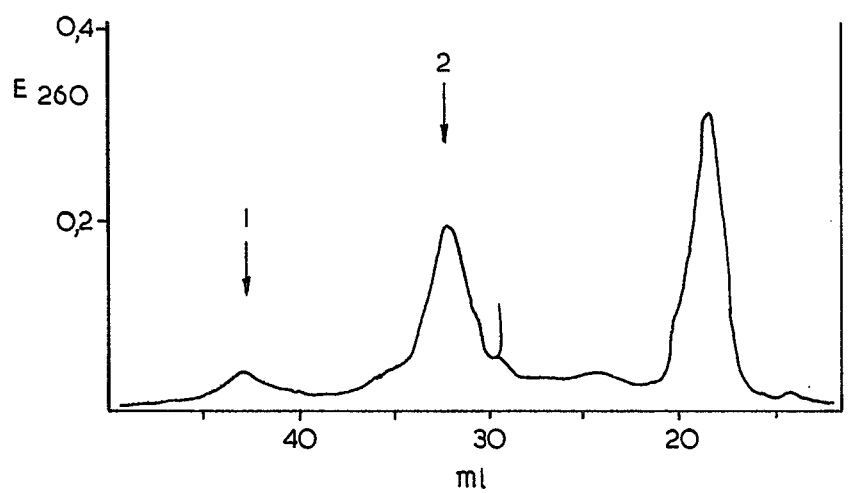

Samples of low-molecular RNA were applied onto analytic gels and preparative gels, and subjected to preparative gel electrophoresis. The voltage gradient in the preparative gel was about 4V per cm. The pumping rate of the auxiliary flow of elution buffer, passing in the direction opposite to the direction of electrophoresis, was about 1.5 ml. per hour. The sum of the pumping rates of the elution buffers was 6 ml. per hour. About 50 $\mu$g of RNA was loaded on the analytical gel and about 150 $\mu$g of RNA was loaded on the perparative gel. The upper graph of FIG. 3 shows the variations in the extinction in the analytic gel, and the lower graph of FIG. 3 shows the variations in the extinction in the elution buffer. The resolving power has not deteriorated noticeably by the elution, and the peaks in the preparative pattern are symmetrical.

EXAMPLE III

Samples of high-molecular nucleolar RNA were loaded on extremely soft 2.20% polyacrylamide gels. The gels were polymerized on glassfiber-paper discs (Whatman GF/C). About 6 $\mu$g of RNA was loaded on the analytic gel, and about 24 $\mu$g of RNA on the preparative gel.

Figure 4:
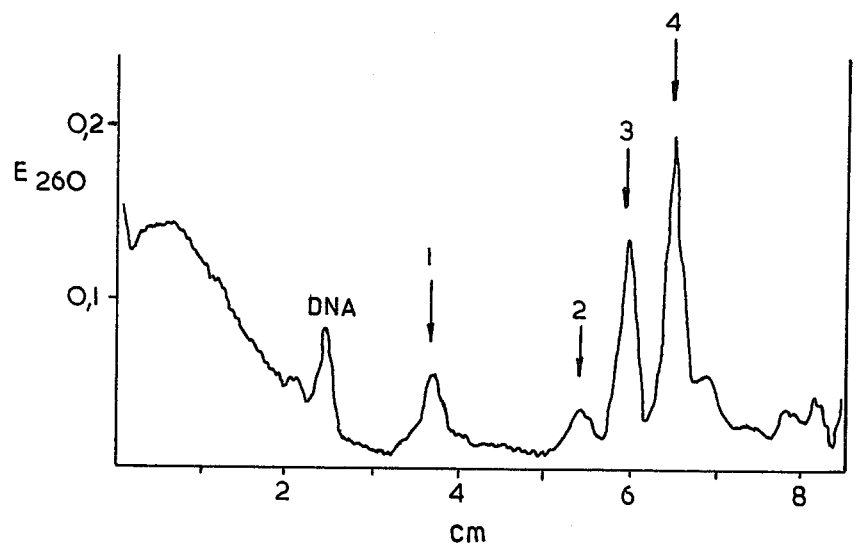
Figure 4:
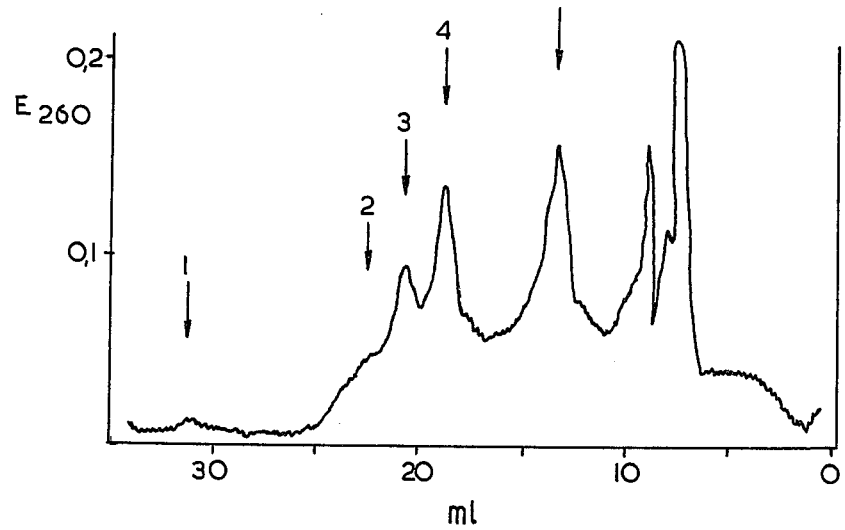
Figure 5:
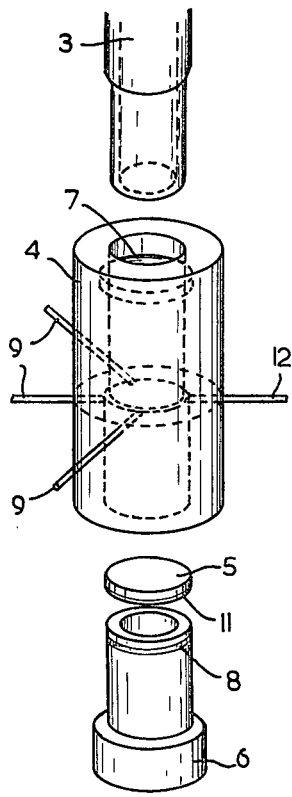
FIG. 5 shows an exploded view of part of the apparatus.

In the upper graph of FIG. 4 the variation in the extinction in the analytic gel is shown, and in the lower graph of FIG. 4 the variation in the extinction in the elution buffer is shown.

The support of the gels by the elution chamber and glassfiber-paper appears to be suitable to produce a good elution with a very soft gel. Otherwise the relatively high base line between the peaks in the preparative pattern are not caused by a bad resolution but by materials in the gel itself, which also give extinction phenomena.

I claim:

1. Electrophoresis apparatus, comprising a tubular member having first and second ends for receiving a column of gel, means defining an elution chamber at the first end of the tubular member, primary inlet duct means for passing buffer solution into the elution chamber, and outlet duct means for discharging buffer solution from the elution chamber and so disposed with respect to the primary inlet duct means that buffer solution passes from the primary inlet duct means to the outlet duct means substantially perpendicular to the central axis of the tubular member, the chamber-defining means comprising a plate-form body of solid but porous material having two main surfaces extending substantially perpendicular to the central axis of said tubular member, and the apparatus also comprising auxiliary inlet duct means for passing an auxiliary flow of buffer solution into the elution chamber through that main surface of the plate-form body which is further from the second end of the tubular member, and a layer of porous material between the elution chamber and the auxiliary inlet duct means, the porous material of said layer having a higher flow resistance to buffer solution than the porous material of the plate-form boyd.

2. Apparatus as claimed in claim 1, wherein the plate-form body is a glass frit.

3. Apparatus as claimed in claim 3, wherein the layer of porous material is a glass frit.

4. Apparatus as claimed in claim 4, wherein the plate-form body and the layer of porous material are sintered together.

5. Apparatus as claimed in claim 1, wherein the plate-form body is sealed to said tubular member by means of a layer of vulcanized 6. material adhered to the plate-form body.

7. Apparatus as claimed in claim 1, wherein the plate-form body is sealed to said auxiliary inlet duct means by means of a layer of vulcanized elastic material adhered to the plate-form body.

7. Apparatus as claimed in claim 7, wherein the plate-form body and the auxiliary inlet duct means are fitted in a cylindrical housing member and the layer of vulcanized elastic material establishes a seal between the plate-form body and the housing member.

8. Electrophoresis apparatus, comprising a tubular member having first and second ends for receiving a column of gel, and means defining an elution chamber at the first end of the tubular member, the chamber-defining means comprising a plate-form body of solid but porous material having two main surfaces, one main surface of the plate-form body being directed towards the tubular member, and the apparatus also comprising duct means for delivering buffer solution into the elution chamber by way of the other main surface of the plate-form boyd, and a layer of porous material between the elution chamber of the duct means, the porous material of said layer having a higher flow resistance to buffer solution than the porous material of the plate-form body.

9. Apparatus as claimed in claim 8, wherein the plate-form body is a glass frit.

10. Apparatus as claimed in claim 9, wherein the layer of porous material is a glass frit.

11. Apparatus as claimed in claim 10, wherein the plate-form body and the layer of porous material are sintered together.

12. Apparatus as claimed in claim 9, wherein the plate-form body is sealed to said tubular member by means of a layer of vulcanized elastic material adhered to the plate-form body.

13. Apparatus as claimed in claim 11, wherein the plate-form body and the duct means are fitted in a cylindrical housing member and the layer of vulcanized elastic material establishes a seal between the plate-form body and the housing member.

14. A method of constructing electrophoresis apparatus, wherein a layer of elastic material is applied to a plate-form body of solid but porous material, the elastic material is vulcanized, and the plate-form body is brought into contact with one end of a tubular member, the vulcanized elastic material establishing a seal between the plate-form body and the tubular member.

15. A method as claimed in claim 13, wherein the plate-form body has two main surfaces, one of which is brought into contact with said one end of the tubular member and the other of which is brought into contact with duct means for delivering buffer solution into the plate-form body, and the vulcanized elastic material establishes a seal between the plate-form body and the duct means.

16. Apparatus as claimed in claim 1, wherein the tubular member is of circular internal cross section.

17. Apparatus as claimed in claim 6, wherein the elastic material is silicone rubber.

18. Apparatus as claimed in claim 7, wherein the elastic material is silicone rubber.

19. Apparatus as claimed in claim 8, wherein the housing member is of circular internal cross-section.

20. Apparatus as claimed in claim 9, wherein the tubular member is of circular internal cross-section.

21. Apparatus as claimed in claim 11, wherein the elastic material is silicone rubber.

22. Apparatus as claimed in claim 12, wherein the housing member is of circular internal cross-section.

23. A method as claimed in claim 13, wherein the elastic material is silicone rubber.

* * * * *